United States Patent [19]

Brown

[11] Patent Number: 5,358,847
[45] Date of Patent: Oct. 25, 1994

[54] METHOD OF SCREENING FOR HUMAN SPERM ABNORMALITIES AS PART OF A REGIMEN FOR ASSESSING FERTILIZING CAPACITY BASED UPON REDUCED RATES OF CHROMATIN DECONDENSATION AND DNA SYNTHESIS

[76] Inventor: David B. Brown, 1216 Pin Oak, Dickinson, Tex. 77539

[21] Appl. No.: 781,357

[22] Filed: Oct. 24, 1991

[51] Int. Cl.$^5$ .............................................. C12Q 1/68
[52] U.S. Cl. ...................................... 435/6; 435/806; 435/810; 935/77
[58] Field of Search .................. 435/6, 91, 91.2, 806, 435/810; 536/27, 23.1; 935/77

[56] References Cited

FOREIGN PATENT DOCUMENTS 87-228385/32 4/1985 PCT Int'l Appl. .
90-077026/11 1/1988 PCT Int'l Appl. .
90-206641/27 7/1990 PCT Int'l Appl. .

OTHER PUBLICATIONS

Dadoune, J. P. (1991) Contracept. Fertil. SEx, vol. 19 (10), pp. 833–839.
Ibrahim, M. E. et al. (1988) Archives of Andrology, vol. 21(2), pp. 129–134.
Brown et al. (1991), *J. Exp. Zool.*, 258:263–272.
Ohsumi et al. (1988), *Gamete Res.* (U.S.A.) 20(1):1–9.
Brown, D., Press Release and Poster Presentation, Dec. 10, 1990–30th Annual Meeting of the American Society of Cell Biology in San Diego, Ca.
Brown et al. (1987), *J. Exp. Zool.*, 242(2):215–231.
Gordon et al. (1985) *Exp. Cell Res.* 157(2):409–418.
Brown et al. (1990) *J. Cell Biol.* 111:115a.
Longo (1985), *Biology of Fertilization*, 3:250–298.
Vodyanoy et al. (1983), *Science*, 220:719–721.
Longo et al. (1978), *Current Top. in Dev. Biol.*, 12(6):149–184.
Zirkin et al. 91985), *Gamete Research*, 11:349–365.
Perreault et al. 91984), *Development Biology*, 101:160–167.
Kasinsky et al. 91985), *The Journal of Experimental Zoology*, 234:33–46.
Yanagimachi et al. (1976), *Biology of Reproduction*, 15:471–476.
Overstreet et al. (1980), *Fertility and Sterility*, 33(5):534–542.
Wolf et al. (1982), *Journal of Andrology*, 3:445–451.
Laskey et al. (1989), *Science*, 246:609–614.
Lohka (1989), *Journal of Cell Science*, 92:131–135.
Fang et al. (1991), *Cell*, 66:731–742.
Kasinsky (1989) In: Histones and Other Basic Nuclear Proteins, *Specificity and Distribution of Serum Basic Proteins*, pp. 73–150, CRC Press, Boca Raton, Fla., eds. L. Hnilica, G. Stein and J. Stein.
Webster et al. (1990), In: The Handbook of the Laboratory Diagnosis and Treatment of Infertility, *The Infertility Evaluation*, pp. 1–9, CRC Press, eds. B. Keel and B. Webster.
Wolgemuth (1983), *Mechanism and Control of Animal Fertilization*, (9):415–452.
Ohsumi et al. (1988), *Gamete Research* 20:1–9.
Lohka et al. (1988), *Experimental Cell Research*, 179:303–309.

*Primary Examiner*—Margaret Parr
*Assistant Examiner*—Lisa Arthur
*Attorney, Agent, or Firm*—Arnold, White & Durkee

[57] ABSTRACT

A method for determining the capacity of a human sperm to fertilize a human egg is described by assessing sperm activation events in an in vitro assay using *Xenopus laevis* frog egg extract. Fertilizing capacity is assessed as a comparison of sperm decondensation, DNA synthesis and/or sperm recondensation as between a test sperm sample sperm and a sperm sample from a proven fertile human male. The method employs results from the in vitro assay to also determine relative sufficiency or insufficient of a sperm sample for fertilizing a human egg in human couples with a history of a diagnosed "unexplained infertility" from standard infertility diagnostic tests. The method may also be used to screen human sperm donors in human artificial insemination programs. A fixed-slide cytoprep sperm analysis of decondensed sperm chromatin, as between a sperm test sample and a sperm sample from a proven fertile human male, may also be used to confirm in vitro decondensation results of the infertility or fertility of a particular human male. A kit is also provided for testing male sperm samples for human egg fertilizing capacity.

32 Claims, 3 Drawing Sheets

METHOD OF SCREENING FOR HUMAN SPERM ABNORMALITIES AS PART OF A REGIMEN FOR ASSESSING FERTILIZING CAPACITY BASED UPON REDUCED RATES OF CHROMATIN DECONDENSATION AND DNA SYNTHESIS

BACKGROUND OF THE INVENTION

1. Field of the Invention

The present invention relates to the field of diagnostic tests for determining if a human male is infertile. More specifically, the present invention provides a method for identifying infertile males by assessing the ability of a particular human sperm sample to fertilize a human egg. The invention also relates to the field of screening protocols, as a method for screening human sperm samples for use in human fertilization is also provided. The invention also relates to the field of diagnostic kits, as a kit for detecting male infertility is also disclosed.

2. Description of the Related Art

Approximately one in six couples find themselves involuntarily infertile. This translates to between two and four million couples in the United States alone. Although numerous tests are available for diagnosing infertility problems, five to ten percent of all couples that seek medical treatment are diagnosed with what is described clinically as "unexplained infertility".

The term "unexplained infertility" is applied to virtually any clinically inexplicable failure of a male and female couple to conceive after extensive fertility testing of both partners reveals no identifiable cause for the couples infertility. After exhausting all available infertility tests with both male and female samples and other recognized infertility evaluations (i.e., female post-coital tests, timed endometrial biopsy, hysterosalpingogram, laparoscopy, male, "normal" sperm analysis, with sperm counts greater than 20 million/ml on at least two occasions, total sperm numbers of 40 million or more, sperm motility greater than 60%, and normal morphology in more than 60% of the sperm[8], and the couple has had a history of involuntary infertility for at least 2 years, a human couple is diagnosed simply as "unexplainably infertile." Such couples historically continue to undergo invasive, protracted and expensive testing in pursuit of a definitive diagnosis of the cause for their infertility.

One typical fertility test for human males is the sperm penetration assay (SPA).[12-14] The SPA tests the activation of a human sperm nucleus following entry into a fertilized egg by a determination of the percentage of eggs that are penetrated by the sperm (as determined by counting the eggs that contain decondensed or activated sperm nuclei). In general, this assay is designed to test the sperm's ability to get its nucleus into the egg. However, this protocol is not used nor may it be used to indicate the efficiency of the sperm decondensation process. During the SPA, the egg (for example, the commonly used hamster egg) routinely becomes bound with a large number of sperm that do not enter the egg and thus do not decondense. Thus, using this assay, one cannot tell a non-decondensed sperm (because it has become bound to the egg) apart from a sperm that has entered the egg and not decondensed as a result of not responding to the egg "activation" signals.

In some cases, the present inventor have observed a zero SPA score may not be reflecting the penetration capabilities of a particular sperm, but instead may reflect the sperm's inability to decondense.

Various techniques have been devised by researchers for using permeabilized sperm incubated in frog egg extracts to study sperm activation events. For example, using *Xenopus laevis* frog sperm incubated in Rana pipiens frog egg extract[1] and using human sperm incubated in *Xenopus laevis* frog egg extract.[2,5] It has been observed that a normal (i.e., of proven human egg fertilizing capacity) human sperm nucleus becomes "activated" upon entry into a frog egg cytoplasm experimentally.[2,5]

The "activation" of a normal human sperm has been reported in preparations of *Xenopus laevis* frog egg extract, which is reportedly attributable to the presence of "factors" in the frog egg extract itself.[5] These activation "factors" in *Xenopus laevis* frog egg extract have been the focus of much investigation by the present inventor and others, and have facilitated the general characterization of "activation" events of normal human sperm (such as the events of the sperm nuclear chromatin decondensation-recondensation cycle and DNA synthesis),[2,5] as well as a "molecular" understanding of the "activation" events.[19-21]

While the experimental model of *Xenopus Laevis* egg extract has been described which relates in general to the events of "normal" human sperm chromatin decondensation after activation,[2,5] the efficiency of the decondensation process has not been described as pertinent to the sperm's fertilizing capacity. Nor is a diagnostic tool for determining or elucidating a particular cause of "unexplained" human male infertility using relative sperm "activation" events been characterized.

Additionally, analysis of the particular onset or duration of, for example, sperm decondensation or sperm recondensation, or the amount of, for example, DNA synthesis, indicators of human male infertility or human sperm capacity to fertilize a human egg, has not been described or suggested in any of the literature. The use of mammalian eggs as a means to obtain extract to follow the sperm activation events has not been possible because it is difficult, if not impossible, to obtain enough extract to examine mammalian fertilization.[6,18]

Biological models for assessing human male fertility have not been established which employ sperm decondensation, recondensation and DNA synthesis events as a diagnostic tool. Moreover, the failure of currently available experimental and clinically accepted tests to examine the relative rate and degree of activity during sperm "activation events", as between "normal" human sperm and sperm with unknown fertilizing capacity, prevents the discovery of the differences which the present inventor have found definitive of the cause of some couples inability to successfully conceive.

An alternative method for diagnosing some cases of "unexplained infertility" through a system which was relatively non-invasive, and which provided for a rapid and accurate prognostic indicator of a human sperm samples' fertilizing capacity for a human egg, would save many currently "unexplained infertile" couples continued expense and invasive, sometimes uncomfortable testing.

SUMMARY OF THE INVENTION

The present inventor has defined a prognostic indicator for human male fertility which effectively assesses the ability of a particular human sperm sample to fertilize a human egg. Specifically, the inventor describes a method wherein a sperm sample's capacity for fertilizing a human egg is determined through the analysis and comparison of sperm molecular "activation" events (i.e., decondensation, DNA synthesis and recondensation) as between sperm samples obtained from a human male of unproven fertility/infertility and a human male of proven fertility. Special application of the present invention is disclosed by the inventor as a method whereby the small percentage of even the most exhaustively and undefinitively diagnosed "infertile couples" may discover the cause of their infertility.

The present invention provides a method for determining the capacity of a human sperm sample to fertilize a human egg. The method requires a comparative analysis of particular sperm "activation" events as between a human patient sperm sample and sperm sample from a human male of proven fertility.

In one particular embodiment of the present invention, an in vitro method for accessing fertilizing capacity of human sperm for a human egg is provided. This method comprises obtaining a human sperm sample and isolating a number of sperm therefrom to provide a test sample, obtaining a human sperm sample from a male of proven fertility and isolating an equal number of sperm to provide a control sample, permeabilizing the sperm of the test sample and the control sample to provide a permeabilized sperm test sample and a permeabilized sperm control sample, reducing the permeabilized sperm test sample and the permeabilized sperm control sample to provide a reduced sperm nuclei test sample and a reduced sperm nuclei control sample, incubating a volume of the reduced sperm nuclei test sample and an equal volume of the reduced sperm nuclei control sample in a *Xenopus laevis* frog egg extract, monitoring the sperm nuclei test sample and sperm nuclei control sample for chromatin decondensation, DNA synthesis and chromatin recondensation activation events in the presence of a detectable labeling compound, and determining differences between the test sample and the control sample activation events to assess the fertilizing capacity of the test sperm sample. According to this particular embodiment, a test sample demonstrating decreased efficiency of chromatin decondensation, DNA synthesis or chromatin decondensation relative to the control sperm sample identifies human sperm having a reduced capacity for fertilizing a human egg.

In a most particularly preferred embodiment, the onset of chromatin decondensation or chromatin recondensation are the parameters within which differences relative to the control sample are assessed. In this embodiment, the onset of chromatin decondensation after the onset of chromatin decondensation of the control sample, or an onset of chromatin recondensation after the onset of chromatin recondensation of the control sample defines a human sperm having a reduced capacity for fertilizing a human egg.

In still another particular embodiment of the present invention, a method for diagnosing infertility in a human male of unexplained infertility is provided. This method comprises obtaining a sperm sample from a human male of unexplained infertility to provide a test sample, obtaining a sperm sample from a human male of proven fertility to provide a control sample, isolating a number of sperm from the test sample and an equal number of sperm from the control sample to provide an assay test sample and an assay control sample, permeabilizing an equal number of the sperm in the assay test sample and the assay control sample in a lysolecithin-containing medium to provide a permeabilized test sperm sample and a permeabilized control sperm sample, reducing a number of the permeabilized test sperm and an equal number of control sperm in Xenopus extract isolation medium (XEIM) containing dithiothreitol to provide a reduced sperm nuclei test sample and a reduced sperm nuclei control sample, incubating an amount of the reduced sperm nuclei test sample and an equal amount of the reduced sperm nuclei control sample in a volume of *Xenopus laevis* frog egg extract which includes a detectable labeling compound, monitoring the nuclei of the test sample and the control sample for chromatin decondensation for at least an about 15 minute incubation period, and comparing the test chromatin decondensation to the control chromatin decondensation.

According to this method, a test sample demonstrating 20% (++) or more decondensed sperm nuclei (i.e., 80% of control) relative to the control sample after an at least 15 minute incubation period is diagnostic of infertility in the human male of previously unexplained infertility.

A reduced amount of sperm decondensation in a test sperm sample is thus indicative of a human sperm inadequacy as the cause of infertility in the human male.

For both of the aforegoing methods, the amount of test and control sperm chromatin sample incubated in the *Xenopus laevis* frog egg extract is most preferably about 200,000 sperm/200 $\mu$l of the *Xenopus laevis* egg extract. Most preferably, the reduced sperm nuclei test sample and the reduced sperm nuclei control sample are to be first incubated with a detectable labeling compound, such as $^3$H-TTP. For example, the sperm are most preferably to be incubated at about 19° C. in 200 $\mu$l of the *Xenopus laevis* frog egg extract which contains, for example, $^3$H-TTP, with the labeled $^3$H-TTP being included at a concentration of about 80 $\mu$Ci/ml of the *Xenopus laevis* frog egg extract. Most preferably, an incubation of the sperm nuclei test sample and sperm nuclei control sample with the $^3$H-TTP is conducted for about 2 hours at about 19° C.

A 20% (i.e., 80% of control) or more decrease in test sperm DNA synthesis as compared to a control sample is indicative of a human sperm inadequacy as the cause of infertility in the human male.

In a most preferred aspect of the methods described above, the permeabilized test sperm and the permeabilized control sperm are reduced in XEIM containing about 50 mM dithiothreitol for about 45 minutes at a temperature of between about 0° C. to 4° C., otherwise described as "on ice."

A patient having "unexplained infertility" for purposes of the presently disclosed methods are male patients whose sperm sample demonstrated normal total sperm count, sperm volume, sperm concentration and sperm morphology, as outlined for "normality" by W. H. O.,[18] standards, for a proven fertile human male.

Specific control sperm characteristics defined from proven fertile males include a sperm concentration of at least 20 million/ml and a total sperm number of at least 40 million. Thus, for purposes of the present description of the invention, the test sperm sample will have been evaluated and determined to demonstrate a concentration of at least 20 million/ml and a total sperm number of at least 40 million.

Where control sperm is obtained immediately after ejaculation, the additional parameter of sperm motility may be examined, with a comparison therein being made to test sperm sample, again where the test sperm sample is obtained immediately after ejaculation. Where sperm motility is an available evaluating criteria, a sperm motility as described below would be characteristic of the human sperm test sample from a patient of unexplained infertility (i.e., within "normal" parameters). Criteria of semen sample "normality" as set forth in the World Health Organization (1987)[8] include the following.

| CRITERIA | |
|---|---|
| Volume | 2.0 ml or more |
| pH | 7.2–7.8 |
| Sperm Concentration | $20 \times 10^6$ or more |
| Total Sperm Count | $40 \times 10^6$ spermatozoa or more |
| Motility | 50% or more with forward progression or 25% or more with rapid linear progression within 60 minutes after collection |
| Morphology | 50% or more with normal morphology (oval-shaped head with regular outline and acrosomal cap covering more than ⅓ of the head surface; midpiece about 7–8 μm standard; and tail uncoiled, at least 45 μm in length |
| White Blood Cells | Fewer than $1 \times 10^6$/ml |
| Zinc (total) | 2.4 micromolar or more/ejaculate |
| Citric Acid (total) | 52 μmol (10 mg) or more/ejaculate |
| Fructose (total) | 13 micromolar or more/ejaculate |
| MAR Test | Fewer than 10% spermatozoa with adherent particles |
| Immunobead Test | Fewer than 10% spermatozoa with adherent beads |

Most preferably, chromatin decondensation as part of the described method is monitored closely for about 10 minutes, with close attention being drawn to the time of test sample chromatin decondensation onset, as well as the relative percentage of sperm nuclei showing chromatin decondensation observed in the test sample relative to that observed in the control sample.

The control samples are stored as semen from proven fertile males obtained fresh on the day of assay. Stored sperm samples may be refrigerated at about 4° C. without significant loss of activity. The present inventor has found that control semen samples refrigerated at 4° C. may be stored without significant loss of sperm activation capacity for up to 30 days and sperm isolated therefrom for use in the present method. Semen samples from unproven males may similarly be stored at 4° C. for future testing purposes. Alternatively, semen samples may be stored frozen for up to 1 year without significant loss of sperm activation capacity.

In an even more preferred embodiment of the claimed method, prior to permeabilizing the test and control sperm samples, the test semen sample and control semen sample are to be washed in a nuclear isolation medium consisting of about 200 mM sucrose, about 2.4 mM MgCl₂, about 10 mM Tris HCl and about 5 mM maleic acid and a pH of about 7.4. All test and control semen samples must be washed at least once to obtain an at least partially isolated sperm sample.

Cytoprep analysis of the test sample has also been found to be confirmatory of the results obtained in the present methods. Cytoprep analysis may be prepared from an aliquot of the test and control "incubation" of sperm at any time point. Most preferably, the cytoprep analysis is to be prepared from an aliquot obtained at 15 minutes incubation (for "smear" of sperm nuclei analysis, a measure of decondensation relative to control).

A test sperm sample which demonstrates about 80% or less the total number of smeared sperm nuclei of the control (described in the examples), (prepared from sperm sample obtained after an about 15 minute incubation period), is diagnostic of a infertile human male. A cytoprep analysis of the number of smeared sperm nuclei after an about 15 minute incubation period may therefore be used either alone as an independent diagnostic test for human male infertility or as a confirmatory test to confirm assay results determined on the basis of the percentage of chromatin decondensation relative to a control sample after an about 15 minute incubation period. A volume of the original test and control sperm incubation sample is obtained and used to prepare the cytoprep analysis. A cytoprep analysis provides a permanent record of the decondensation events observed.

Permeabilization of the test sample and control sample sperm most preferably is accomplished by incubating an equal number of the sperm test sample and the sperm control sample in a medium containing about 0.05% lysolecithin and about 1 μg/ml soybean trypsin inhibitor for about 5 minutes at about 22° C.

In still another aspect of the present invention, a method for screening a prospective human sperm donor for in vitro fertilization of a human egg is provided. This screening method comprises obtaining a sperm sample from the prospective human sperm donor to provide a test sample, obtaining a sperm sample from a proven fertile human male to provide a control sample, permeabilizing a number of test sample sperm and an equal number of control sample sperm in a medium containing about 0.05% lysolecithin and a serine protease inhibitor, such as about 1 μg/ml soybean trypsin inhibitor (a protease inhibitor which will inactivate proteases in the preparation) to provide permeabilized human test sperm and permeabilized human control sperm, reducing a number of the permeabilized test sperm and an equal number of the permeabilized control sperm in a XEIM containing dithiothreitol to provide a reduced test sperm sample and a reduced control sperm sample, incubating the reduced test sperm sample and the reduced control sperm sample in a *Xenopus laevis* frog egg extract containing a detectable labelling compound, monitoring sperm decondensation, recondensation and DNA synthesis of the test sample and the control sample for at least about 3 hours in a volume of *Xenopus laevis* frog egg extract, comparing the sperm decondensation, recondensation and DNA synthesis demonstrated in the control sperm sample to the test sperm sample, and identifying a fertile prospective human sperm donor where the amount of test sperm decondensation, recondensation or DNA synthesis is at least 80% of the decondensation, recondensation or DNA synthesis of the control sperm sample, respectively.

In a most preferred aspect of this described method, the test sperm and the control sperm sample are reduced in a XEIM containing about 50 mM dithiothreitol for about 45 minutes at about 0° C. to 4° C. Most preferably, the detectable labelling compound used is ³H-TTP or tritiated thymidine.

The present invention also provides a method for diagnosing infertility in a human male partner of an unexplained infertile human couple. This method consists essentially of preparing a modified *Xenopus laevis* frog egg extract capable of sequentially inducing at least three sperm activation events, said human sperm activation events including sperm chromatin decondensation, DNA synthesis and sperm chromatin recondensation, obtaining and preparing a sperm sample from the human male partner of the unexplained infertile human couple to provide a test sperm sample, obtaining and preparing a human sperm sample from a proven fertile human male to provide a control sperm sample, permeabilizing a number of the test sperm sample and an equal number of the control sperm sample in a nuclear isolation medium containing about 0.05% lysolecithin and about 1 μg/ml soybean trypsin inhibitor for about 5 minutes at about 22° C., washing the permeabilized test sperm sample and the control sperm sample in a volume of nuclear isolation medium containing about 3% bovine serum albumin, pelleting and washing a second time the permeabilized test human sperm sample and the control sperm sample in a volume of nuclear isolation medium containing about 0.4% bovine serum albumin, reducing a number of the washed test sperm sample and an equal number of the control sperm sample in a volume of XEIM. The XEIM most preferably contains about 10 mM Tris-HCl, about 1.5 mM $MgCl_2$, about 100 mM KCl and about 50 mM dithiothreitol, wherein the concentration of control sperm and test sperm, respectively, in the medium is about 25,000 sperm/ml, for about 45 minutes at between about 0° C. to about 4° C.

Next, the method includes labeling the permeabilized (and reduced) test sperm sample and the control sperm sample in the presence of a detectable labeling compound contained within a volume of Xenopus laevis frog egg extract, wherein a concentration of about 200,000 sperm is combined with about 200 μl of Xenopus laevis frog egg extract containing the detectable labeling compound at a concentration of about 80 μCi/ml, monitoring sperm decondensation, DNA synthesis and chromatin recondensation of the test sperm sample and the control sperm sample in a volume of Xenopus laevis frog egg extract for at least about 3 hours, comparing the sperm decondensation, DNA synthesis, and chromatin recondensation of the test sperm sample to the control sperm sample, comparing the sperm decondensation, DNA synthesis and chromatin recondensation of the test sperm sample to the control sperm sample, and diagnosing infertility in the human male partner of the unexplained infertile human couple where the test sample demonstrates reduced chromatin decondensation, reduced DNA synthesis or reduced sperm chromatin recondensation relative to the control sperm sample.

Most preferably, a "reduced" chromatin decondensation, DNA synthesis or recondensation is defined as 80% or less the activity demonstrated in the control sperm sample from sperm of a proven fertile human male over an equal incubation period and under the same sperm in vitro conditions.

A diagnostic kit for screening human males for infertility is also disclosed. In a preferred embodiment of the diagnostic kit comprises a carrier means adapted to receive at least four container means therein, a first container means containing a volume of dithiothreitol, a second container means containing a volume of lysolecithin, a third container means containing a Xenopus laevis frog egg extract, a fourth container means containing a control sample having a capacity for human sperm activation from a proven fertile human male, and at least two container means suitable for including therein a volume of up to 1 ml of a human sperm sample. The kit also most preferably includes a written instruction sheet defining the diagnostic test steps to be employed for screening human males for infertility using the kit.

The Xenopus laevis frog egg extract of the kit is to be prepared fresh, and will remain stable and sufficiently active for use in the screening assay for at least about 2–3 days stored at about 0° C. to 4° C. ("on ice"). Alternatively, the kit may be shipped without the Xenopus laevis frog egg extract included therein, with the Xenopus laevis egg extract provided upon a proposed date of assay to assure maximum freshness.

The Xenopus laevis frog egg extract may most preferably also be treated with a protease inhibiting substance(s) effective for reducing loss of sperm activation potential of the extract. Such will enhance the shelf life of the kit and the assay in general as described in all of the embodiments disclosed herein.

In still another embodiment of the described kit, reagents and materials for the preparation of fixed cytoprep slides of both a test sperm sample and a control sperm sample is provided. For such an embodiment, the kit would also comprise at least two glass slides and at least two filter cards. Even more preferably, the kit includes at least 6 glass slides and at least 6 filter cards. Thus, cytoprep analysis may be performed for the test sperm sample and control sperm sample at the 15 minute incubation time (for smeared sperm nuclei analysis), at the 2 hour incubation time (to determine and compare relative DNA synthesis), and at the 3 hour incubation time (to determine and compare recondensation).

The kit in still another embodiment may comprise an autoradiography emulsion, an autoradiography developer, an autoradiography fixer and a Giemsa blood staining solution. The kit may also optionally comprise a container means including a volume of bovine serum albumin.

As used in the description of the present invention, a human male of "proven" fertility is defined as a male whose sperm is known to be capable of fertilizing a human egg, for example, a sperm sample from a human male who has sired a child (a "proven breeder"). Even more fully defined, a proven fertile human male for purposes of describing the present invention is defined as a human male who has recently achieved a pregnancy within 12 months of their partner ceasing contraception.

The term "unexplained infertility" as used in the description of the present invention as pertains to a male partner of an "undiagnosed infertile" couple, is defined as a human male whose sperm sample demonstrates normal sperm concentration (count), sperm mobility, sperm morphology, characteristic of a proven fertile human male[8] and having been involuntarily infertile for at least 2 years.

The proven fertile male sperm samples need not necessarily be tested for sperm motility following ejaculation as stored sperm may be used in the assay with equal efficacy. However, the control samples are examined for normal sperm count and sperm morphology.

Abbreviations used throughout the description of the present invention include:
NIM=Nuclear Isolation Medium
XEIM=Xenopus extract isolation medium
TTP=Methyl-$^3$H thymidine 5'-triphosphate
SPA=Sperm Penetration Assay
HSAA=Human Sperm Activation Assay
GIFT=Gammete Fertilization Transfer
DTT=Dithiothreitol

BRIEF DESCRIPTION OF THE DRAWINGS

FIGS. 1E–1H are phase contrast micrographs. FIGS. 1a–1d are bright field micrographs of Giemsa-stained nuclei. FIG. 1G is a Giemsa-stained autoradiograph. 1A–1E: Time zero. 1B,1F: 15 minutes incubation. 1C,1G: 2 hour incubation. 1D,1H: 3 hour incubation. Bar, 10 μm.

FIGS. 4A–4F. Bright field photographs of Giemsa-stained autoradiographs of sperm nuclei following 2 hours of incubation in frog egg extract. 4A. Fertile control, decondensed labelled sperm nucleus (96%). FIGS. 4B–4F show examples of the variable decondensation and labelling observed in Patient #15 sperm nuclei. 4B. Nuclei neither decondensed, nor labelled (41%). 4C. Nucleus decondensed and labelled (14%). 4D. Nucleus decondensed and unlabelled (8%). 4E. Nucleus decondensed, smeared and unlabelled (7%). 4F. Nucleus decondensed, smeared and labelled (30%). Bar, 10 μm. Micrographs were photographed at 800×magnification using a Zeiss Photomicroscope III.

DETAILED DESCRIPTION OF THE PREFERRED EMBODIMENTS

The present invention provides a unique method for assessing the fertilizing capacity of a sample of human sperm. A method for using such a method as a diagnostic screening test for human couples having an undiagnosed inability to conceive despite exhaustive standard fertility screening procedures, is also provided.

The "fertilizing" capacity of a sample of human sperm obtained from any particular male has been shown by the inventor to, on some occasions, change from incapable of supporting fertilization to fully capable of fertilizing the egg sufficient to allow the development of the fertilized egg to a two cell stage embryo, using the present methods. Therefore, the present invention also provides for a system of evaluating a potential sperm donor's sperm sample for fertilizing capacity prior to the use of the sperm for use in the artificial insemination of a female.

A diagnostic kit for evaluating the fertilizing capacity of a human sperm sample for a human egg is also provided.

Lysolecithin employed in permeabilizing sperm samples was obtained from Sigma Chemical Company (L-α-Lysophosphatidylcholine, Sigma No. L-4129, from egg yolk, type 1, approximate purity 99%). Bovine serum albumin was also obtained from Sigma (BSA, Sigma No. A-7906, 98–99% albumin). Soybean trypsin inhibitor was obtained from Boehringer Mannheim, No. 109 886. Dithiothreitol, DTT, (also called Cleland's reagent) was obtained from Calbiochem, No. 233155.

For cytoprep analysis, filter cards were obtained from Shandon Inc., (SCA-0005). Giemsa stain was obtained from Baker (Catalog No. M,708-01). For autoradiography, the Kodak NTB2 autoradiography emulsion was obtained from International Biotechnologies, Inc. (IBI, No. 1654433). Kodak developer was obtained from International Biotechnologies, Inc. as well (D-19, CAT 146-4593). Kodak fixer was also obtained from this source (CAT No. 197-1746).

The detectable labeled compound $^3$H-TTP was obtained from I.C.N. (Catalog No. 24044H, Irvine, Calif.).

Various chemicals employed in preparing the nuclear isolation medium, XEIM and Barth's Medium, such as $MgCl_2$, KCl, $MgSO_4$, $Ca(NO_3)_2$, $CaCl_2$, Tris-HCl. Penicillin and streptomycin were obtained from Gibco. Cysteine-HCl, maleic acid and sucrose were obtained from Sigma Chemical Company.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are presented to describe preferred embodiments and utilities and to satisfy "best mode" requirements of the present invention, but should not be construed as limiting the claims thereof.

EXAMPLE 1

Preparation of *Xenopus laevis* Frog Egg Extract

The present example is provided to define the most preferred embodiment of the particular *Xenopus laevis* frog egg extract found to provide the enhanced method of determining/detecting the cause of unexplained infertility in a human male. The herein described optimal method for isolating the egg extract provides for the sequential potent and definitively observable inducement of the three events characteristic of sperm activation, which are 1) sperm nuclear chromatin decondensation, 2) DNA synthesis and 3) sperm nuclear chromatin recondensation.

Pretreatment of human sperm at a concentration of about 25,000 sperm/μl in the XEIM described herein, containing 50 mM DTT for about 45 minutes on ice, before mixing with the *Xenopus laevis* frog egg extract was found to enhance the decondensation and DNA synthesis events.

To promote oocyte maturation, ovulation and egg laying, adult female *Xenopus laevis* frogs were injected with 500 IU of human chorionic gonadotropin in the morning and evening of the day preceding the experiment. Mature eggs were collected and dejellied with 2% cysteine-HCl, pH 7.6. The eggs were then rinsed and incubated for about between 30 minutes to 1 hour at room temperature (22° C.) in Barth's medium comprised of 88 mM NaCl, 1.0 mM KCl, 0.83 mM $MgSO_4$, 0.34 mM $Ca(NO_3)_2$, 0.41 mM $CaCl_2$, 7.5 mM Tris-HCl, pH 7.6, 10 μg/ml penicillin, 10 μg/ml streptomycin and 2.4 mM $Na(CO_3)_2$. The eggs were washed three times in XEIM. Excess buffer was removed and the eggs lysed by centrifugation at 10,000 g, 4° C., for 15 minutes in a swinging bucket rotor. The resulting middle layer between the lipids and the egg pellet was removed from the centrifuge tube, recentrifuged, and the resulting middle layer used as the stock extract solution. The extract was stored on ice until used for the HSAA.

EXAMPLE 2

Method for Diagnosing Unexplained Infertility as a Dysfunction of Human Sperm Preparation The present example is provided to demonstrate a most preferred method for diagnosing unexplained infertility from a sperm sample.

All semen donors whose samples will be employed as "control" samples (proven fertile males as determined from the successful conception of at least 1 child) will have abstained from ejaculation for 2 at least days prior to the collection of the semen samples. Semen samples will be obtained by masturbation and stored in a refrigerator at about 4° C. until the date of assay. Such refrigerated sperm samples stored at 4° C. from proven fertile males for up to month (30 days) were found to respond the same as did sperm freshly collected from the same male on the date of testing in the human sperm activation assay described herein.

Semen samples from unexplained infertility patients will be obtained from various infertility clinics throughout the country and the HSAA will be performed as described below. We will purchase normal, control semen samples from fertile males. Fresh samples are not needed for the HSAA, as stored semen samples from a fertile male were found to respond the same in the human sperm activation assays as did sperm collected from the same fertile male on the day the assay was performed, even after a 4° C. storage of up to a month (data not shown).

On the day that the diagnostic method is to be performed, the samples are incubated for 30 minutes at 37° C.; each sample is then suspended in 10 ml of nuclear isolation medium (NIM, 200 mM sucrose, 2.4 mM $MgCl_2$, 10 mM Tris-Hcl and 5 mM maleic acid, pH 7.4). A sperm count is taken and an aliquot (containing 20 million sperm) is pelleted in a centrifuge for 10 minutes at 400 Xg, then resuspended in 10 ml of NIM containing 0.05% lysolecithin and 1 µg/ml soybean trypsin inhibitor. The mixture is kept at room temperature for 5 minutes and the sperm repelleted as before, then washed, first in NIM with 3% BSA and then with NIM containing 0.4% BSA, as described by Lohka and Masui[1]. Sperm will finally be suspended in Xenopus Extract Isolation Medium (XEIM, 10 mM Tris-HCL, pH 7.5, 1.5 mM $MgCl_2$, 100 mM KCl and 50 mM DTT) at a concentration of 25,000 sperm/µl and kept on ice (between 0° C. and 4° C.) for 45 minutes before mixing with the frog egg extract. This XEIM (DTT) pretreatment was found to enhance the decondensation and DNA synthesis events. Such may be the result of reducing the protamines that in mammalian sperm are cross-linked by intermolecular disulfide bonds.[9]

Sperm contain "intermediate" protamines that are not cysteine rich, so the frog egg extract lacks the reducing factor(s) found in mammalian eggs that are required for reducing the disulfide bridges of the human sperm.[10,11] The disulfide bonds were therefore reduced experimentally by including DTT in a pretreatment incubation medium described as a XEIM. The preincubation of the test sperm sample and the control sperm sample also was found by the present inventor to enhance the decondensation and DNA synthesis "activation" events.

The sperm permeabilization is required in order for the sperm nuclei to be able to contact the egg extract, thus inducing sperm activation.

Egg Extract Isolation

To promote oocyte maturation, ovulation and egg laying, adult female *Xenopus laevis* frogs are injected with 500 IU (in a volume of 500 µl) of human chorionic gonadotropin in the morning and evening of the day preceding the experiment. Mature eggs are then collected and dejellied with 2% cysteine-HCl, pH 7.6. The eggs are then rinsed and incubated for one hour at room temperature in Barth's medium comprised of 88 mM NaCl, 1.0 mM KCl, 0.83 mM $MgSO_4$, 0.34 mM $Ca(NO_3)_2$, 0.41 mM $CaCl_2$, 7.5 mM Tris-HCl, pH 7.6, 10 µg/ml penicillin, 10 µg/ml streptomycin and 2.4 mM $Na(CO_3)_2$. The eggs are washed three times in Xenopus Extract Isolation Medium (XEIM, 10 mM Tris-HCL, pH 7.5, 1.5 mM $MgCl_2$, 100 mM KCl and 50 mM DTT). Excess buffer is removed and the eggs lysed by centrifugation at 10,000 g, 4° C., for 15 minutes in a swinging bucket rotor. The resulting middle layer between the lipids and the egg pellet is removed from the centrifuge tube, recentrifuged, and the resulting middle layer used as the stock extract solution. The extract is stored on ice until used for the HSAA.

The procedure described by Lohka and Masui for the preparation of the egg extract was modified, as the *Rana pipiens* egg extract prepared and used therein employed an isolation medium included 250 mM sucrose (not needed in the claimed system), 200 mM KCl (the present assay uses 100 mM for optimal results), 1.5 mM $MgCl_2$, 2.0 mM Beta-mercaptoethanol (the present assay uses a much higher concentration of a different reducing agent called dithiothreitol or DTT, for the same reasons that were discussed above for the DTT pretreatment of the sperm) and 10 mM tris-HCl at pH 7.5 (the same concentration is used).

Human Sperm Activation Assay (HSAA)

Permeabilized, reduced sperm from the normal control and infertility patients are mixed separately with *Xenopus laevis* frog egg extract at a concentration of 150,000 sperm/150 µl of extract. The permeabilized reduced sperm is incubated at 19° C. in 200 µl of extract containing $^3$H-TTP at a concentration of 80 µCi/ml. Chromatin decondensation, DNA synthesis and chromatin recondensation is then evaluated.

Phase-contrast microscopy is used to assess chromatin decondensation and recondensation. Aliquots (5 µl) are taken, placed on glass slides, and covered with glass coverslips at 5 and 10 minutes and at 3 hours following the addition of the sperm to the frog egg extract. At the 5 and 10 minute time point, the percentage of sperm that have decondensed is determined (50 sperm per sample are scored during the assay at both the 5 and 10 minute time points). Between 95–100% of the control sperm have normally decondensed within 5–10 minutes.

Recondensation of chromatin of the sperm nuclei is determined at the 3 hour time point (again, 50 sperm will be scored per sample). Recondensation is typically observed in 95–100% of the control sperm. DNA synthesis in the sperm nuclei is assessed using a 50-µl aliquot taken at the 2 hour time point and diluted with 50 µl of phosphate-buffered saline. The sperm is then affixed to glass slides by centrifugation, dried, and fixed for 5 minutes in Carnoy's fixative (three parts ice-cold methanol to one part glacial acetic acid). These fixed cytopreps are then dipped in 42° C. Kodak nuclear track emulsion (NTB-2), stored at 4° C. for two weeks, and then following development (2 minutes in Kodak D-19 developer followed by 2 minutes in Kodak Fixer) are Giemsa stained through the emulsion (45 minutes in 2.5% Giemsa stain in phosphate buffer). Approximately 200 nuclei were scored for labelling and the results with control sperm (% of the nuclei showing label above background) compared to those with the patients' sperm.

Cytopreps of the sample sperm specimens (and the corresponding control sperm specimens) were also prepared at the 15 minute time point, and the relative amount of chromatin smearing assessed (an indicator of the extent of chromatin decondensation). Cytopreps prepared at the three hour time point were prepared as a measure of chromatin recondensation. The cytopreps were prepared and fixed as previously described followed by Giemsa staining without autoradiography. All microscopy is done using a Leitz Orthoplan microscope.

All samples from the infertility patients that are found to respond normally in the HSAA are reported as normal to the infertility clinic that sent the sample. Any abnormal responses will also be reported to the infertility clinic that sent the sample. However, before releasing the results to the patient, we will require another sample be sent so that we can verify that the abnormal response is repeatable. Thus, a patient that has a normal response in the HSAA will know the results within 3 weeks of our receiving their sample. A patient that demonstrates an abnormal response will know the results from HSAA within 3 weeks.

EXAMPLE 3

Clinical Testing For Unexplained Infertile Male Sperm Samples

The present example provides a clinical study wherein 20% of sperm samples obtained from the male partner of a couple previously diagnosed as unexplicably infertile, was diagnosed as relating to sperm inadequacy for "sperm activation".

MATERIALS AND METHODS

Unexplained Infertility Patients

For the inventor's clinical studies, a couple was diagnosed as having unexplained infertility, when the following conventional tests have been completed without finding a cause for the couple's infertility; the female partner will have undergone complete infertility evaluations including postcoital tests (to rule out sperm motility loss in cervical mucus); a timed endometrial biopsy (to exclude luteal phase defect); a hysterosalpingogram (to establish tubal patency,) and laparoscopy (to rule out pelvic pathology); in the male partner, semen analysis would have been normal on two occasions with sperm concentrations greater than 20 million/ml, total sperm numbers of 40 million or more, sperm motility greater than 60% and normal morphology in more than 60% of the sperm.[8] The inexplicably infertile couples must also have been involuntarily infertile for over two years.

In this study, sperm was obtained from 15 unexplained infertility patients that have been involuntarily infertile for more than 5 years (average of 7.3 years, range of 5 to 10 years). All of the semen samples from the unexplained infertility patients that were analyzed in this study had normal sperm concentrations, total sperm counts, and morphology.

Human Sperm Preparation

All semen donors abstained from ejaculation for 2 days prior to the collection of the semen samples that were obtained by masturbation.

Semen samples from 15 unexplained infertility patients were obtained at the time of the regularly scheduled procedures at an interfertility clinic (e.g., sperm penetration assay, SPA; fertilization-embryo transfer, IVF-ET; and gamete intrafallopian transfer, GIFT). A portion of the sample not used for these procedures was used for the HSAA. These samples were kept in a 4° C. refrigerator for up to 7 days for parallel weekly assays on samples collected throughout the week. Semen samples from 15 fertile males were stored from 1-7 days mimicking the storage conditions of the semen samples from the unexplained infertility patients. Fresh samples are not needed for the HSAA, as stored semen samples from a fertile male were found to respond the same in the human sperm activation assays as did sperm collected from the same fertile male on the day the assay was performed, even after 4° C. storage of up to a month (data not shown).

On the day of the diagnostic test, semen samples were incubated for 30 minutes at 37° C.; each sample was then suspended in 10 ml of nuclear isolation medium (NIM, 200 mM sucrose, 2.4 mM $MgCl_2$, 10 mM Tris-HCl and 5 mM maleic acid, pH 7.4). A sperm count was taken and an aliquot (containing 20 million sperm) was pelleted in a centrifuge for 10 minutes at 400 Xg, then resuspended in 10 ml of NIM containing 0.05% lysolecithin and 1 µg/ml soybean trypsin inhibitor.

The mixture was kept at room temperature for 5 minutes and the sperm repelleted as before, then washed, first in NIM with 3% BSA and then with NIM containing 0.4% BSA, substantially as described by Lohka and Masui.[1] Sperm were finally suspended in Xenopus Extract Isolation Medium (XEIM, 10 mM Tris-HCL, pH 7.5, 1.5 mM $MgCl_2$, 100 mM KCl and 50 mM DTT) at a concentration of 25,000 sperm/µl and kept on ice for 45 minutes before mixing with the frog egg extract. This XEIM (DTT) pretreatment was found to enhance the decondensation and DNA synthesis events (unpublished observations), presumably by reducing the protamines that in mammalian sperm are cross-linked by intermolecular disulfide bonds.[9]

*Xenopus laevis* sperm contain "intermediate" protamines[10] that are not cysteine rich,[11] so the frog egg extract lacks the reducing factor(s) found in mammalian eggs that are required for reducing the disulfide bridges of the human sperm; the disulfide bonds will thus be reduced experimentally.

*Xenopus laevis* Egg Extract Isolation

To promote oocyte maturation, ovulation and egg laying, adult female *Xenopus laevis* frogs were injected with 500 IU of human chorionic gonadotropin in the morning and evening of the day preceding the experiment. Mature eggs were collected and dejellied with 2% cysteine-HCl, pH 7.6. The eggs were then rinsed and incubated for one hour at room temperature in Barth's medium comprised of 88 mM NACl, 1.0 mM KCl, 0.83 mM $MgSO_4$, 0.34 mM Ca $(NO_3)_2$, 0.41 mM $CaCl_2$, 7.5 mM Tris-HCl, pH 7.6, 10 µg/ml penicillin, 10 μg/ml streptomycin and 2.4 mM Na(CO₃)₂. The eggs were washed three times in XEIM. Excess buffer was removed and the eggs lysed by centrifugation at 10,000 g, 4° C., for 15 minutes in a swinging bucket rotor. The resulting middle layer between the lipids and the egg pellet was removed from the centrifuge tube, recentrifuged, and the resulting middle layer used as the stock extract solution. The extract was stored on ice until used for the HSAA.

Human Sperm Activation Assay (HSAA)

Permeabilized sperm from the normal control and infertility patients were mixed separately with frog egg extract at a concentration of 150,000 sperm/150 μl of extract. The permeabilized sperm were incubated at 19° C. in extracts containing ³H-TTP at a concentration of 80 μCi/ml. Chromatin decondensation, DNA synthesis and chromatin recondensation were evaluated. Phase-contrast microscopy was used to assess chromatin decondensation and recondensation. Aliquots (5 μl) were taken, placed on glass slides, and covered with glass coverslips at 5 and 10 minutes and at 3 hours following the addition of the sperm to the frog egg extract.

a. Sperm Decondensation

At time intervals of 5 and 10 minutes, the percentage of sperm that had decondensed (FIG. 1B) was determined. Between 95–100% of the control sperm were normally decondensed within 5 minutes. At the 10 minute time point, between 95–100% normally have the appearance of the nucleus shown in FIG. 1B. At the 3 hour time point, it was determined if the sperm nuclei had recondensed their chromatin as is seen by the smaller nucleus shown in FIG. 1D when compared to the nucleus shown in FIG. 1B. Recondensation was typically observed in 95–100% of the control sperm.

b. DNA Synthesis

DNA synthesis in the sperm nuclei was assessed using 20 μl aliquots taken at the 2 hour time point and diluted with 50 μl of phosphate-buffered saline. The sperm were then affixed to glass slides by centrifugation, dried, and fixed for 5 minutes in Carnoy's fixative (three parts ice-cold methanol to one part glacial acetic acid). These fixed cytopreps were then dipped in 42° C. Kodak nuclear track emulsion (NTB-2), stored at 4° C. for two weeks, and then following development were Giemsa stained through the emulsion.

c. Sperm Recondensation

Figure 1A:
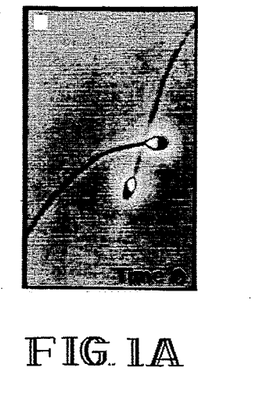
FIGS. 1A–1H. Pictorial representation of permeabilized human sperm incubated in frog egg extract. Micrograph photographed at 800×magnification using a Zeiss Photomicroscope III.
Figure 1B:
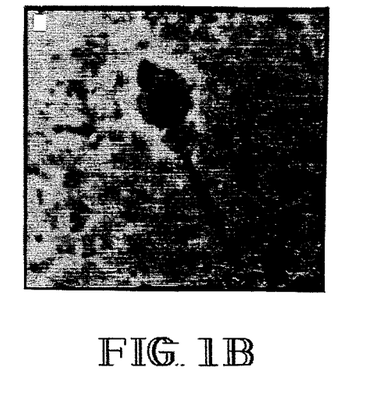
Figure 1C:
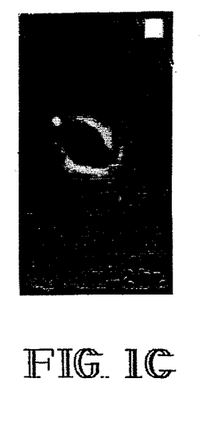
Figure 1D:
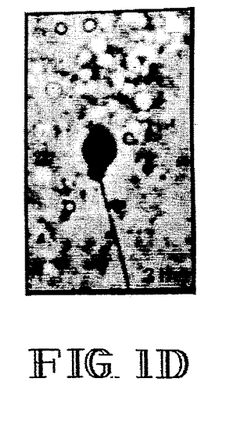
Figure 1E:
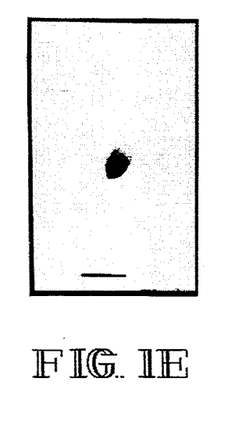
Figure 1F:
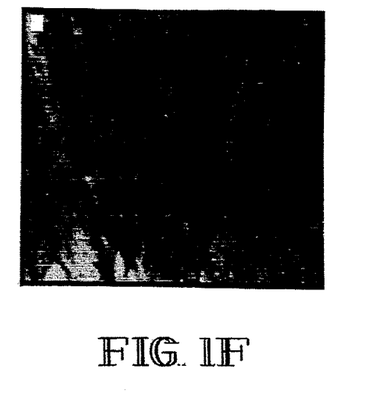
Figure 1G:
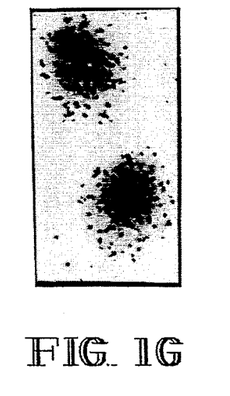
Figure 1H:
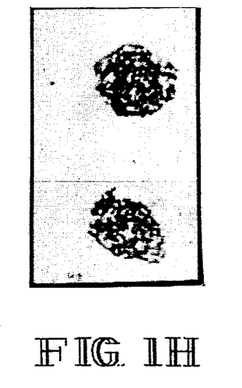

Cytopreps were also prepared at the three hour time point to see if the chromatin had recondensed to the level shown in FIG. 1H.

The cytopreps were prepared and fixed as previously described followed by Giemsa staining without autoradiography. All microscopy was done using a Leitz Orthoplan microscope. The micrographs in FIGS. 1A–4F, 1H were photographed at 800×magnification using a Zeiss Photomicroscope III. Two hundred nuclei were scored for labelling and the results with control sperm (% of the nuclei showing label above background) compared to those with the patients' sperm.

RESULTS

Normal Sperm (Control) Response in the HSAA

A pictorial representation of a normal response of permeabilized human sperm to the frog egg extract is shown in FIGS. 1A–4F. The sperm nuclei shown in FIGS. 1A–1D and 1E–1H were photographed (800×magnification) and printed at the same magnification, with the bar representing 10 μm. Phase contrast microscopy was used when photographing the nuclei shown in FIGS. 1A–1D, while FIGS. 1E–1H are bright field photographs of Giemsa-stained cytopreps, with the nuclei shown in FIG. 1G being Giemsa-stained autoradiographs. Permeabilized sperm without extract treatment are shown in FIGS. 1A and 1E. Following a 5 minute incubation in the frog egg extract, greater than 90% of the sperm are decondensing. After a 10–15 minute incubation in the extract, greater than 95% of the sperm have completely decondensed nuclei. A typical completely decondensed sperm nucleus is shown in FIG. 1B. We have observed that at the 15 minute time point, the sperm nuclei do not remain intact during the cytocentrifugation procedure used when making cytopreps; the nuclei become smeared onto the glass slide (FIG. 1F). Following a 2 hour incubation in the frog egg extract, the sperm nuclei have begun to recondense their chromatin. Notice the decrease in size of the sperm nucleus shown in FIG. 1C as compared to the nucleus shown in 1B. The recondensed sperm nuclei also withstand the cytocentrifugation procedure, (note intact nuclei in FIG. 1G). The labelling of these nuclei indicates that they have undergone DNA synthesis. Typically, >95% of the control nuclei are labelled following a 2 hour incubation in frog egg extract containing ³H-TTP, while >95% are fully recondensed following a 3 hour incubation. Examples of recondensed nuclei are shown in FIGS. 1D and 1H.

Use of the HSAA in the Analysis of the Sperm Obtained From Fertile Males and Unexplained Infertility Patients In this study, sperm samples were obtained from 15 unexplained infertility patients and 15 fertile males and prepared for use in the HSAA as described in the Methods. In each HSAA, sperm from a fertile male (previously shown to produce sperm that has a normal response in the (HSAA) was also assayed as a parallel control. A rating system (Table 1) was developed to compare the HSAA responses of the control sperm sample to the sperm samples obtained from 15 unexplained infertility patients and 15 fertile males.

TABLE 1

| Human Sperm Activation Assay Rating Scheme | | | | |
|---|---|---|---|---|
| | % of Control | | | |
| | <40 | 40–60 | 60–80 | 80–100 |
| % Decondensing at 5 Minutes | — | + | ++ | +++ |
| % Decondensing at 10 Minutes | — | + | ++ | +++ |
| % Synthesizing DNA at 2 Hours | — | + | ++ | +++ |
| % Recondensing at 3 Hours | — | + | ++ | +++ |

A range of about 60–80% (or less) will be considered an "abnormal" response.

The results of the pilot study are shown in Table 2. The data summarized in Table 2 demonstrates that three of the sperm samples from the infertility patients responded abnormally in the HSAA, whereas all sperm from known fertile men using conventional fertility measuring responded normally in the assay.

TABLE 2

| Human Sperm Activation Assay Pilot Study Results | | | | |
|---|---|---|---|---|
| | Decondensation (5 Minutes) | Decondensation (10 Minutes) | DNA Synthesis (2 Hours) | Recondensation (3 Hours) |
| Fertile Males 1–15 | +++ | +++ | +++ | +++ |

TABLE 2-continued

Human Sperm Activation Assay Pilot Study Results

| | Decondensation (5 Minutes) | Decondensation (10 Minutes) | DNA Synthesis (2 Hours) | Recondensation (3 Hours) |
|---|---|---|---|---|
| Infertility Patients 1-3, 5, 7-14 | +++ | +++ | +++ | +++ |
| Infertility Patient 4 | + | ++ | +++ | +++ |
| Infertility Patient 6 | +++ | +++ | — | +++ |
| Infertility Patient 15 | + | + | + | ? |

EXAMPLE 4

Diagnosis of Male Infertility and Delayed Sperm Decondensation

The present example is presented to demonstrate the use of the herein disclosed method for tracing a couple's infertility to a particular insufficiency of the male sperm decondensation process after entry into the egg cytoplasm. These data demonstrate that less (at least 38% to 45% less) patient sperm nuclei had decondensed relative to control sperm nuclei (after a 5-minute incubation) was characteristic of sperm obtained from the male partner of an "unexplained infertile" couple.

Sperm from patient number 4 sperm, although scoring normal (60%) in the sperm penetration assay (SPA), had a diminished decondensation response (50% decondensed after 5 minutes of incubation in extract), by which normal human sperm demonstrated a 95% decondensation. After a 10-minute incubation, only 80% of the patient's number 4 sperm had decondensed. The HSAA for patient's number 4 was repeated using the excess sperm from an unsuccessful GIFT attempt (4 eggs transferred), which resulted in a finding that 60% of these sperm decondensed after 5 minutes of incubation in the extract. After the same incubation period with normal (i.e., known fertile) sperm, 98% sperm decondensation was observed. Following a 10-minute incubation in the egg extract, 90% of the patient's sperm had decondensed, with 98% of the control sperm being decondensed.

When new samples of patient's number 4 sperm were obtained for use in the HSAA at 4, 11, and 13 months following the initial analyses, this patient's sperm responded normally in the HSAA when compared to the control (fertile). During the time period where the patient's sperm was responding normally in the HSAA, and IVF-ET attempt resulted in a successful pregnancy, however, the pregnancy ended with a spontaneous miscarriage at six weeks of pregnancy.

The five different semen samples (two showing abnormal HSAA responses, three responding normally) as obtained from patient 4 resulted in three normal HSAA results for reasons which are unknown at the present time.

HSAA may thus also be used to predict sperm efficacy when used for in vitro fertilization assays.

The sperm from the particular male No. 4 in this study is a member of a couple that had been trying to conceive for ten years and at the present, with the exception of the presently disclosed method, had presently been determined to be normal in every test performed.

EXAMPLE 5

Diagnosis of Male Infertility and Reduced Labeled Sperm Nuclei

The present example is provided to demonstrate the observance of a reduced number of labeled sperm nuclei following a 2 hour incubation in a *Xenopus laevis* frog egg extract as an indicator because of infertility in a male from a prior "unexplained infertile" human couple.

Figure 2A:
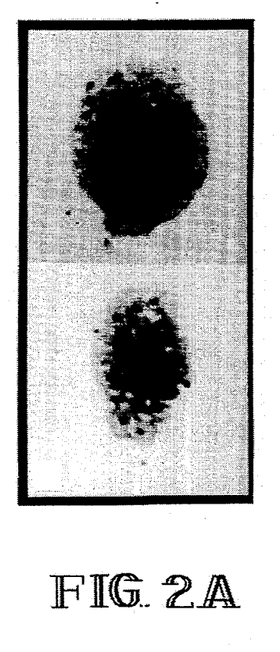
FIGS. 2A and 2B. Bright field photographs of Giemsa-stained autoradiographs of sperm nuclei following 2 hours of incubation in frog egg extract. 2A. Fertile control labelled nuclei. 2B. Patient #6 unlabelled nuclei. Bar, 10 μm. Micrographs were photographed at 800×magnification using a Zeiss Photomicroscope III.
Figure 2B:
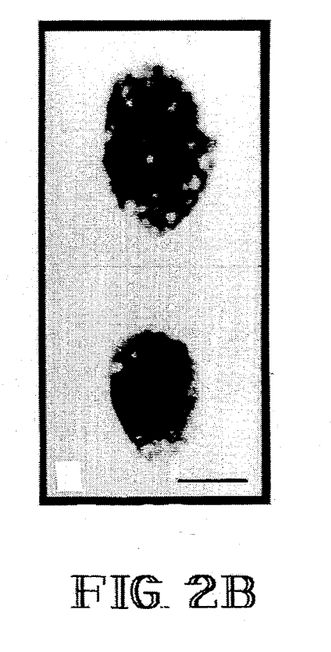

A sperm sample was obtained from patient No. 6 as described in example 1. This particular sperm sample was found to decondense and recondense in a normal fashion. However, only 27% of the sperm nuclei were found to be labeled following autoradiography, while 100% of the control sperm nuclei were found to be labeled. Autoradiographies of typical labeled controlled nuclei and unlabeled patient nuclei are shown in FIGS. 2A and 2B, respectively.

Patients No. 6 was the male partner in a "unexplained infertile" categorized human couple who had a history of attempting to achieve conception for 8 years.

The present example demonstrates that a reduction in the percentage of labeled sperm nuclei of at least 73% (i.e., 27% labelled nuclei relative to control (100%)) provides a positive diagnosis of human male infertility according to the presently disclosed methods. However, the estimate of what will be the "indicator" cutoff as <80% of the DNA synthesis observed in control nuclei is also considered a positive indication of male infertility.

EXAMPLE 6

Sperm Nuclei Smearing After Cytocentrifugation and Sperm Decondensation

The present example is provided to demonstrate the diagnosis of a previously unknown cause of infertility in a couple through observation of the percentage of decondensation of sperm nuclei as indicated through sperm nuclei "smearing" after cytocentrifugation of a sample, and phase contrast miscroscophy observations at 5 and 10 minutes, as well as a reduced synthesis of DNA in the sperm nucleus of the patient, as compared to control.

A sample of sperm was obtained from a patient No. 15 and processed substantially as described in example 1. The sperm sample from patient No. 15 responded variably in the rate and extent of decondensation and DNA synthesis. Only 50% of the sperm had decondensed at both the 5- and 10-minute time point with 45% showing partial decondensation and 5% showing full decondensation. The cytopreps from the 15 minute time point are shown in FIGS. 3A-3B.

Figure 3A:
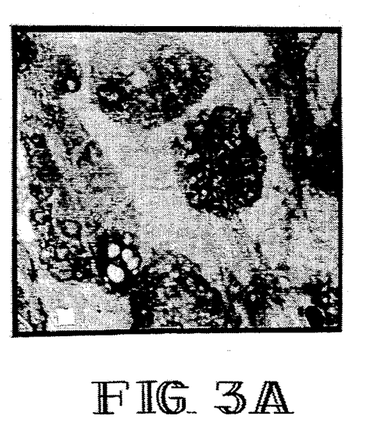
FIGS. 3A and 3B. Bright field photographs of Giemsa-stained sperm nuclei following 15 minute incubations in frog egg extract. 3A. Fertile control, decondensed and smeared nuclei. 3B. Patient #15, 3 nuclei that are neither smeared nor decondensed by a decondensed smeared nucleus. Bar, 10 μm. Micrographs were photographed at 800×magnification using a Zeiss Photomicroscope III.
Figure 3B:
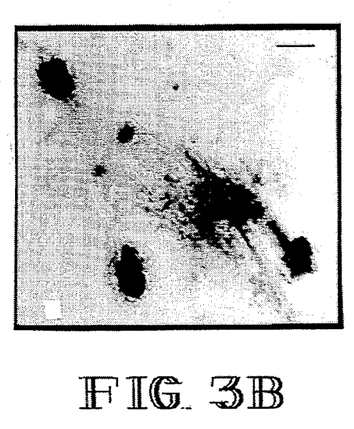

In FIG. 3A, is shown the typical smearing of the sperm nuclei seen from control normal (known fertile) sperm in the HSAA. In FIG. 3B are shown sperm nuclei from patient No. 15, with three intact sperm nuclei and one smeared nucleus. Sperm nuclei that are not decondensing maintain their nuclear structure during cytocentrifugation, while decondensing sperms smear on the glass slide.

Figure 4A:
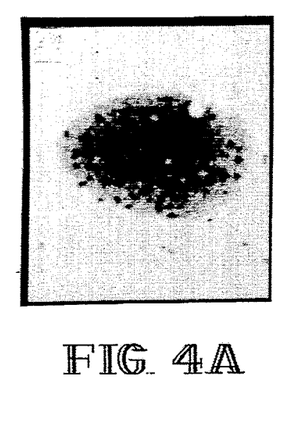
Figure 4B:
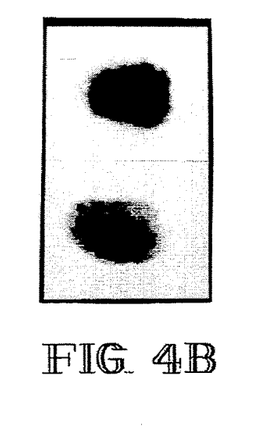
Figure 4C:
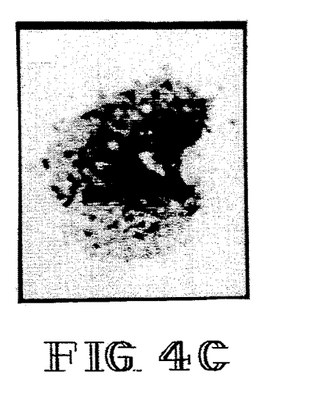
Figure 4D:
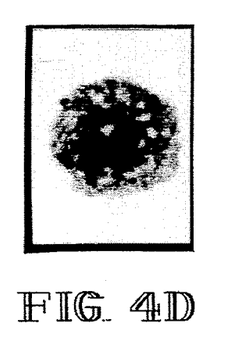
Figure 4E:
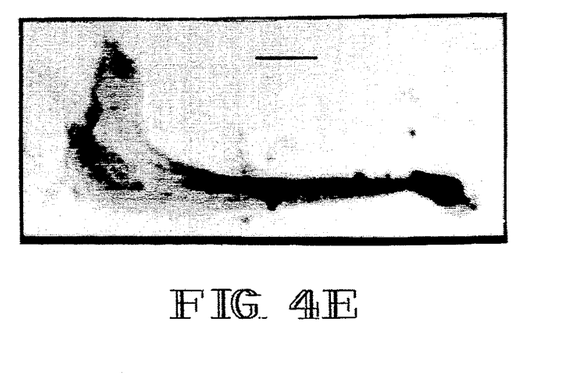
Figure 4F:
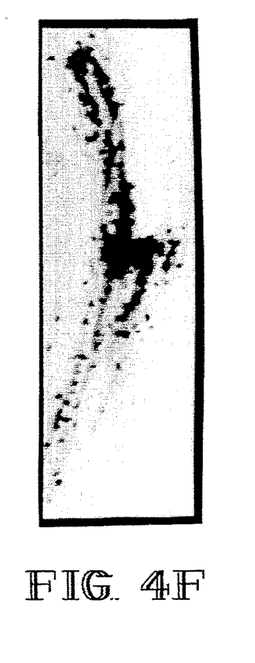

In FIGS. 4A-4F, it is shown the cytoprep-autoradiographies of sperm nuclei from a control fertile male (FIG. 4A) and from patients No. 15 (FIGS. 4B-4F) that had been incubated in egg extract containing tritiated thymidine for 2 hrs. In the control labeled nuclei, 96% were found to be labeled. Nuclei from patient No. 15 demonstrated variable levels of decondensation, with 44% of the nuclei being labeled. 41% of the nuclei were neither decondensed nor labeled (FIG. 4B), 14% were decondensed and labeled (FIG. 4C), 8% were decondensed and unlabeled (FIG. 4D), 7% were smeared and unlabeled (FIG. 4E) and 30% were smeared and labeled (FIG. 4F).

The male and female counterpart of this couple had a history of failure to conceive for a period of seven years. The sperm penetration assay score obtained using patient No. 15 sperm sample was zero. When using donor sperm, the first attempt at artificial insemination of the female of this couple resulted in a pregnancy, indicating that the infertility experienced by the couple was linked to male sperm defect in function, specifically to the poor rate of sperm nuclei decondensation and lower amount of DNA synthesis after fertilization.

PROPHETIC EXAMPLE 7

Proposed Diagnostic Human Sperm Testing Kit

The present prophetic example is provided to demonstrate a preferred embodiment of the proposed diagnostic kit to be used in the clinic or private laboratory to test sperm samples for possible infertility.

The following reagents will be employed in various embodiments of the claimed diagnostic kit.

For Sperm Permeabilization

1. Nuclear Isolation Medium (NIM) 200 mM sucrose, 2.4 mM $MgCl_2$, 10 mM Tris-HCl, and 5 mM maleic acid, pH 7.4.
2. Lysolecithin (L-α-Lysophosphatidylcholine, Sigma, No. L-4129) from egg yolk, Type I, Approx. 99%.
3. Bovine Serum Albumin (BSA) from Sigma, No. A-7906, 98–99% albumin.
4. Soybean Trypsin Inhibitor from Boehringer Mannheim, #109 886.
5. Xenopus Extract Isolation Medium without DTT (DTT added to XEIM less than 24 hours, most preferably less than 1 hour
   prior to using for the permeabilized sperm pretreatment before adding the sperm to the frog egg extract). 1.5 mM $MgCl_2$, 100 mM KCl, and 10 mM Tris-HCl, pH 7.5.
6. Dithiothreitol, DTT, also called Cleland's Reagent, from Calbiochem, 233155.

For Cytopreps

1. Glass Slides.
2. Filter Cards, Shandon Inc., SCA-0005.
3. Giemsa Blood Staining Solution, Baker (#M708-01)

For Autoradiography

1. Kodak NTB2 autoradiography emulsion, International Biotechnologies, Inc. (IBI), #165443.
2. Kodak developer D-19, Cat 146-4593.
3. Kodak fixer, Cat 197-1746.

Frog Egg Extract

*Xenopus laevis* egg extract may be prepared as described in Example 1. The frog extract may be included as part of the diagnostic kit where the diagnostic kit is used within 3 days of the formulation of the egg extract. Alternatively, the *Xenopus laevis* frog egg extract will be prepared fresh on the date of assay, and not transmitted as part of the kit itself. Either a detailed printed description of the protocol for preparing the extract will be provided in the assay kit, or the clinician/physician may obtain a fresh formulated preparation of the frog egg extract, not more than one day prior to the date of assay.

A cytocentrifuge, table top centrifuge and a light microscope equipped with phase contrast objectives will be required as standard laboratory or clinic equipment in order to conduct the sperm fertility assay. The sperm fertility assay most preferable will be conducted under Biosafety Level 2 conditions as standard for the analysis of human tissue.

PROPHETIC EXAMPLE 8

Method for Screening Prospective Sperm Donors for In Vitro Human Fertilization

The present example is provided to outline a method for use in screening human male sperm samples as prospective sperm donors for the in vitro fertilization of human females.

All human samples must be handled according to those laboratory criteria known to those in the art as "Biosafety level 2." Possible test sample and control sample contamination of laboratory personnel with, for example, hepatitis and human immunodeficiency virus will thus be avoided. All samples should be screened for HIV prior to use in an in vitro fertilization attempt, and the sample discarded even if it is demonstrated to have potential human egg fertilizing capacity.

For the described method, a semen sample from a prospective human sperm donor, or from a "panel" (more than one) of prospective human sperm donors, will be obtained and washed to isolate test sperm samples. A control sperm sample will also be prepared from a semen sample obtained from a human male who is of "proven" fertility (sired a child within the preceding 12-month period). A number of sperm from the test sperm sample(s) and an equal number of the control sperm sample will then be permeabilized in a medium containing lysolecithin and soybean trypsin inhibitor, most preferably at a concentration of about 0.05% lysolecithin and 1 μg/ml soybean trypsin inhibitor in an NIM medium. The permeabilized test and control sperm sample will then be reduced in a medium containing dithiothreitol (DTT), most preferably at a concentration of 50 mM DTT as part of the XEIM medium described in Example 1.

The reduced test sperm sample(s) and control sperm sample in equal number are then to be incubated in a detectable labeling compound, such as $^3$H-TTP, for about 5 minutes at 19° C. Most particularly, the concentration of $^3$H-TTP is about 80 μci/ml.

After incubation in the detectable labeling compound, a number of the sperm in the test sperm sample(s) and an equal number of the sperm in the control sperm sample are to be incubated in a volume of *Xenopus laevis* frog egg extract (egg extract defined in Example 1). The sperm activation events of sperm chromatin decondensation, sperm chromatin recondensation and DNA synthesis are then to be monitored in all samples for at least an incubation period of 3 hours.

A prospective human sperm donor for in vitro fertilization of a human egg will be identified in donors whose sperm samples do not demonstrate any abnormality in sperm decondensation, DNA synthesis and sperm recondensation, as compared to the control human sperm sample. A test sperm sample should demonstrate at least 80% the sperm decondensation of a control sample.

Cytoprep analysis of a small volume of sperm incubate from test samples and control samples may be performed to confirm acceptable sperm decondensation rates, DNA synthesis and sperm recondensation rates employing a 15 minute, 2 hour and 3 hour sperm aliquot from the respective incubates.

The method for screening prospective human sperm donors may be used on a large scale inexpensively and using only a small volume of the patient obtained sample, and would be relatively inexpensive and rapid as part of a battery of standard clinical sperm screening routine.

While those of skill in the art will be able to practice the present invention with the aid of the disclosure provided here, the following references may facilitate practice or enhanced understanding of certain aspects. Inclusion of a reference in this list is not intended to and does not constitute an admission that the reference constitutes prior art with respect to the present invention.

The following references are specifically incorporated herein in pertinent part for the particular purposes indicated.

BIBLIOGRAPHY

1. Lohka M. J., Masui Y., (1983) *Science*, 2300:719-721.
2. Brown D. B., Blake E. J., Wolgemuth D. J., Gordon K., Ruddle F. H., (1987) *J Exp Zool*, 242:215-231.
3. Longo F. J., (1973) *Biol. Reprod.* 9:149-215.
4. Longo F. J., Kunkle M., (1978) *Curr. Top. Dev. Biol.*, 12:149-184.
5. Gordon K. Brown D. B., Ruddle F. H., (1985) *Exp. Cell Res.*, 157:409-418.
6. Zirken et al., (1985) *Gamete Res.*, 11:349-365.
7. Brown D. B., Nagamani M. (1990); *J. Cell Biol.* 111:115a.
8. World Health Organization: Appendix 1.A, Normal values of semen variables. In WHO laboratory manual for the examination of human semen and semen-cervical mucus interaction. New York: Cambridge University Press, 1987, p. 27
9. Perreault S. D., Barbee R. R., Slott V. L. (1984), *Dev. Biol.*, 101:160-167.
10. Kasinsky H. E., Huang S. Y., Mann M., Roca J., Subirana J. A. (1985); *J. Exp. Zool.*, 234:33-45.
11. Kasinsky H. E. (1989). Specificity and distribution of sperm basic proteins. In Histones and Other Basic-Nuclear Proteins. Edited by L. S. Hnilica, G. S. Stein and J. L. Stein. Florida, CRC Press Inc. (1989), pp. 73-163.
12. Yanagimachi R., Yanagimachi H., Rogers B. J., (1976) *Biol. Reprod.* 15:471-476, 1976.
13. Overstreet J. W., Yanagimachi K., Katz D. F., Hayashi K., Hanson F. W., (1980) *Fertil. Steril.*, 33:534-542.
14. Wolf D. P., Sokoloski J. E., (1982) *J. Androl.*, 3:445-451.
15. Johnson, L. (1990), Spermatogenesis (Animal Species and Humans). In Gamete Physiology. Edited by R. H. Asch, J. P. Balmaceda and I. Johnston. Norwell, Mass., Serono Symposia, USA, 1990, pp. 3-18.
16. Webster B. W., Cook A. S., Garner C. H. (1990), The infertility evaluation. In Handbook of the Laboratory Diagnosis and Treatment of Infertility. Edited by B. A. Keel and B. W. Webster. Florida, CRC Press Inc., 1990, pp. 1-9.
17. U.S. Congress, Office of Technology Assessment, (May 1988), Infertility: Medical and Social Choices. OTA-BA 358, U.S. Government Printing Office, Washington D.C.
18. Wolgemuth (1983), Synthetic activities of the Mammalian early embryo: Molecular and genetic alterations following fertilization. In: Mechanism and Control of Animal Fertilization. J. F. Hartmann. ed. Academic Press. Inc., New York. p.p. 415-452.
19. Laskey, R. A., Fairman, M. P., and Blow, J. J. (1989), *Science*, 246:609-614.
20. Lohka, M. J. (1989), *J. of Cell Science*, 92:131-135.
21. Fang, F., Newport, J. W. (1991), *Cell*, 66:731-742.

What is claimed is:

1. An in vitro method for screening human sperm for abnormalities as part of a regimen for assessing fertilizing capacity comprising:

obtaining a human sperm sample and isolating a number of sperm therefrom to provide a sperm test sample having a sperm count;

obtaining a human sperm sample from a male of proven fertility and isolating a number of sperm equal to the number in the sperm test sample to provide a sperm control sample having a sperm count;

permeablizing the sperm of the sperm test sample and the control sperm sample to provide a permeablized sperm test sample and a permeablized sperm control sample;

chemically reducing the permeablized sperm test sample and the permeablized sperm control sample in the presence of dithiothreitol to provide a reduced sperm nuclei test sample and a reduced sperm nuclei control sample;

incubating a volume of the reduced sperm nuclei test sample and an equal volume of the reduced sperm nuclei control samples to provide an amount of sperm chromatin sufficient to assess sperm chromatin decondensation in a *Xenopus laevis* frog egg extract;

quantifying the sperm nuclei test sample and the sperm nuclei control sample activation events, first, for chromatin decondensation, and second, for DNA synthesis in the presence of a detectable labeling compound; and determining differences between the sperm test sample and the sperm control sample activation events to assess the fertilizing capacity of the sperm test sample, wherein a sperm test sample demonstrating 80% or less decondensed sperm nuclei or 80% or less DNA synthesis relative to the sperm control sample, identifies abnormal human sperm.

2. A method for screening for abnormal human sperm as part of a regimen for diagnosing infertility in a human male of unexplained infertility comprising:

obtaining a sperm sample from a human male of unexplained infertility to provide a sperm test sample having a sperm count;

obtaining a sperm sample from a human male of proven fertility to provide a sperm control sample having a sperm count;

isolating a number of sperm from the sperm test sample and an equal number of sperm from the sperm control sample to provide an assay sperm test sample and an assay sperm control sample;

permeabilizing an equal number of the sperm in the assay sperm test sample and the assay sperm control sample in a lysolecithin-containing medium to provide a permeabilized sperm test sample and a permeabilized control sample;

chemically reducing a number of the permeabilized sperm test sperm and an equal number of control sperm sufficient to provide an amount of sperm chromatin sufficient to assess sperm chromatin decondensation in a *Xenopus laevis* extract isolation medium containing dithiothreitol to provide a reduced sperm nuclei test sample and a reduced sperm nuclei control sample in a volume of *Xenopus laevis* frog egg extract which includes a detectable labeling compound;

quantifying the nuclei of the test reduced sperm nuclei sample and the control reduced sperm nuclei sample for chromatin decondensation; and comparing the chromatin decondensation in the reduced sperm nuclei test sample to the chromatin decondensation in the sperm control sample;

wherein a sperm test sample demonstrating 80% or less decondensed sperm nuclei as compared to the sperm control sample is characteristic of abnormal human sperm as part of a screening regimen in a human male having unexplained infertility.

3. The method of claim 1 or 2 wherein the volume of the reduced sperm nuclei test and control samples in the *Xenopus laevis* frog egg extract is about 200,000 sperm/200 µl of the *Xenopus laevis* egg extract.

4. The method of claim 1 or 2 wherein the detectable labeling compound is $^3$H-TTP included at a concentration of about 80 µCi/ml of *Xenopus laevis* frog egg extract.

5. The method of claim 4 wherein the reduced sperm nuclei sample and the reduced sperm nuclei control sample are incubated in the presence of $^3$H-TTP for about 2 hours at about 19° C.

6. The method of claim 1 or 2 wherein the permeabilized sperm test sample and the permeabilized sperm control sample are reduced in a *Xenopus leavis* extract isolation medium containing about 50 mM dithiothreitol for about 45 minutes at a temperature of between about 0° C. to 4° C.

7. The method of claim 2 wherein the sperm count, of the sperm test sample from the human male of unexplained infertility is at least above 20 million/ml.

8. The method of claim 1 or 2 wherein the sperm count of the sperm test sample is at least 40 million total sperm.

9. The method of claim 2 wherein chromatin decondensation is monitored for about 10 minutes.

10. The method of claim 1 or 2 wherein the sperm control sample may be stored at 0° C. to 4° C. for up to 30 days before use in the method.

11. The method of claim 1 or 2 wherein the sperm control sample may be stored frozen for up to 1 year.

12. The method of claim 2 wherein the sperm test sample and sperm control sample are washed in a nuclear isolation medium consisting of about 200 mM sucrose, about 2.4 mM MgCl$_2$, about 10 mM Tris HCl, and about 5 mM maleic acid at a pH of about 7.4 before permeabilizing.

13. The method of claim 2 wherein sperm chromatin decondensation is measured after about a 15 minute incubation period.

14. The method of claim 1 or 2 wherein the sperm test sample and sperm control sample are permeabilized in a medium containing about 0.05% lysolecithin and about 1 µg/ml soybean trypsin inhibitor for about 5 minutes at about 22° C.

15. A method for screening human sperm as part of a regimen for selecting prospective human sperm donors for in vitro fertilization of a human egg comprising:

obtaining a sperm sample from a prospective human sperm donor to provide a sperm test sample;

obtaining a sperm sample from a human male of known fertility to provide a sperm control sample;

permeabilizing a number of sperm in the sperm test sample and an equal number of sperm in the sperm control sample in a medium containing lysolecithin and a protease inhibitor to provide permeabilized human test sperm and permeabilized human control sperm;

chemically reducing a number of the permeabilized test sperm and an equal number of the permeabilized control sperm sufficient to assess sperm chromatin decondensation in a *Xenopus laevis* extract isolation medium containing dithiothreitol to provide a reduced test sperm sample and a reduced control sperm sample;

incubating the chemically reduced test sperm sample and the reduced control sperm sample in a *Xenopus laevis* frog egg extract containing a detectable labeling compound;

quantifying first, sperm decondensation and, second, DNA synthesis;

comparing the sperm decondensation and DNA synthesis demonstrated in the reduced control sperm sample to the reduced test sperm sample; and selecting a fertile prospective human sperm donor from a doner whose sperm test sample demonstrates an amount of sperm chromatin decondensation or DNA synthesis greater than 80% of the decondensation or DNA synthesis of the sperm control sample.

16. The method of claim 15 wherein the sperm test sample and sperm control sample are chemically reduced in *Xenopus laevis* extract isolation medium containing about 50 mM dithiothreitol for about 45 minutes at about 0° C. to about 4° C.

17. The method of claim 15 wherein the detectable labeling compound is $^3$H-TTP or tritiated thymidine.

18. The method of claim 15 wherein the lysolecithin is contained at a concentration of about 0.05% and the protease inhibitor is soybean trypsin inhibitor at a concentration of about 1 µg/ml.

19. A method for screening for abnormal sperm as part of a regimen for diagnosing infertility in a human male partner of an unexplained infertile human couple comprising:

preparing a modified *Xenopus laevis* frog egg extract capable of sequentially inducing at least two human sperm activation events, said human sperm activation events including sperm chromatin decondensation and DNA synthesis;

obtaining and preparing a sperm sample from the human male partner of an unexplained infertile human couple to provide a sperm test sample;

obtaining and preparing a sperm sample from a proven fertile human male to provide a sperm control sample;

permeabilizing a number of sperm in the sperm test sample and an equal number of sperm in the sperm control sample in a nuclear isolation medium containing about 0.05% lysolecithin and about 1 microgram/ml soybean tripsin inhibitor for about 5 minutes at about 22° C.;

washing the permeabilized test sperm sample and the permeabilized control sperm sample in a volume of nuclear isolation medium containing about 3% bovine serum albumin;

collating and washing a second time the permeabilized test sperm sample and the permeabilized control sperm sample in a volume of nuclear isolation medium containing about 0.4% bovine serum albumin to provide a washed test sperm sample and a washed control sperm sample;

reducing a number of sperm of the washed test sperm sample and an equal number of sperm of the control washed sperm sample in a volume of Xenopus extract isolation medium including about 50 mM dithiothreitol for about 45 minutes at about between 0° C. to about 4° C. to provide a reduced test sperm sample and a reduced control sperm sample;

labeling the reduced test sperm sample and the reduced control sperm sample in the presence of a detectable labeling compound contained within a volume of *Xenopus laevis* frog egg extract;

monitoring sperm chromatin decondensation and DNA synthesis of the reduced test sperm sample and the reduced control sperm sample in a volume of *Xenopus laevis* frog egg extract for at least about 3 hours;

comparing the sperm chromatin decondensation and DNA synthesis of the reduced test sperm sample to the reduced control sperm sample;

determining the presence of abnormal sperm wherein abnormal sperm in the reduced test sperm sample demonstrate an 80% or less rate of sperm chromatin decondensation and an 80% or less rate of DNA synthesis as compared to the rate of sperm chromatin decondensation and DNA synthesis in the reduced control sperm sample of chromatin decondensation and DNA synthesis as compared to the control sample as part of a screening regimen for diagnosing infertility in the human male partner of the unexplained infertile human couple.

20. The method of claim 19 wherein the detectable labeling compound is $^3$H-TTP contained at a concentration of about 80 $\mu$Ci/ml within a *Xenopus laevis* frog egg extract.

21. A diagnostic kit for determining the presence of abnormal human sperm comprising:
a carrier means adapted to receive at least four container means therein;
a first container means containing dithiothreitol;
a second container means containing lysolecithin;
a third container means containing a *Xenopus laevis* frog egg extract; and
a fourth container means containing a control sperm sample having a capacity for normal chromatin decondensation and DNA synthesis from a proven fertile human male.

22. The kit of claim 21 further comprising a written instruction sheet.

23. The kit of claim 21 wherein the *Xenopus laevis* frog egg extract is stable for at least 48 hours stored at about 4° C.

24. The kit of claim 21 comprising at least 2 glass slides and at least 2 filter cards.

25. The kit of claim 21 comprising at least 6 glass slides and at least 6 filter cards.

26. The kit of claim 21 further comprising an autoradiography emulsion, an autoradiography developer, and an autoradiography fixer.

27. The kit of claim 21 comprising a container means including a volume of bovine serum albumin.

28. The kit of claim 21 comprising a container means of Giemsa Blood Staining Solution.

29. The method of claim 15 wherein sperm chromatin decondensation is determined by observation of sperm chromatin under light microscopy or by visualization with an electron microscope and wherein DNA synthesis is determined by autoradiography.

30. An in vitro method for screening a human sperm sample for abnormalities as part of a regimen for sperm assessing fertilizing capacity of human sperm from a male of unexplained infertility for a human egg comprising:
obtaining a human sperm sample and isolating about 20 million sperm therefrom to provide a sperm test sample;
obtaining a human sperm sample from a male of proven fertility and isolating about 20 million sperm to provide a sperm control sample;
permeabilizing the sperm of the sperm test sample and the sperm control sample to provide a permeabilized sperm test sample and a permeabilized sperm control sample;
chemically reducing the permeabilized sperm test sample and the permeabilized sperm control sample in the presence of dithiothreitol to provide a reduced sperm nuclei test sample and a reduced sperm nuclei control sample;
incubating a volume of the reduced sperm nuclei test sample and an equal volume of the reduced sperm nuclei control sample sufficient to assess sperm chromatin decondensation in a *Xenopus laevis* frog egg extract; and
observing the reduced sperm nuclei test sample and the sperm nuclei control sample for chromatin decondensation after about 15 minutes incubation and for DNA synthesis in the presence of a detectable labeling compound after about 2 hours incubation;
wherein a reduced sperm nuclei test sample demonstrating less than about 80% decondensed sperm nuclei as compared to the reduced sperm nuclei control sample and less than about 80% DNA synthesis as compared to the reduced sperm nuclei control sample determines the presence of sperm abnormalities as part of a regimen for assessing fertilizing capacity of human sperm.

31. An in vitro method for screening human male sperm for the presence of abnormal human sperm comprising:
comparing sperm chromatin decondensation and DNA synthesis in a test sperm sample and in a fertile sperm sample; and
identifying abnormal human sperm in the test sperm sample wherein abnormal human sperm demonstrate less than about 80% chromatin decondensation and less than about 80% DNA synthesis than in the fertile sperm sample.

32. A method for screening human sperm for sperm abnormalities comprising:
processing a human test sperm sample and a human fertile control sperm sample so as to provide a sufficient amount of sperm chromatin from each sample to assess sperm chromatin decondensation in a *Xenopus laevis* frog egg extract; and
comparing the rate of sperm chromatin decondensation and DNA synthesis in the human fertile control sperm sample and the human test sperm sample,
wherein a human test sperm sample having less than about 80% the rate of sperm chromatin decondensation and less than about 80% of the DNA synthesis relative to the human fertile control sperm sample indicates human sperm abnormalities.

* * * * *

UNITED STATES PATENT AND TRADEMARK OFFICE
CERTIFICATE OF CORRECTION

PATENT NO. : 5,358,847
DATED : October 25, 1994
INVENTOR(S) : David S. Brown

It is certified that error appears in the above-indentified patent and that said Letters Patent is hereby corrected as shown below:

Title page, item [57]

In column II of the Abstract, line 18, please delete "in vitro" and substitute -- *in vitro* -- therefor.

In claim 1, column 22, line 13, please delete "in vitro" and substitute --*in vitro*-- therefor.

In claim 5, column 23, line 33, between "nuclei" and "sample" please insert --test-- therefor.

In claim 15, column 24, line 3, please delete "in vitro" and substitute --*in vitro*-- therefor.

In claim 19, column 24, line 67, please delete "tripsin" and substitute --trypsin-- therefor.

In claim 30, column 26, line 8, please delete "in vitro" and substitute --*in vitro*-- therefor.

In claim 31, column 26, line 43, please delete "in vitro" and substitute --*in vitro*-- therefor.

Signed and Sealed this

Twenty-second Day of August, 1995

Attest:

BRUCE LEHMAN

*Attesting Officer*  *Commissioner of Patents and Trademarks*